United States Patent [19]

Bahrmann et al.

[11] Patent Number: 5,410,072

[45] Date of Patent: Apr. 25, 1995

[54] MIXTURES OF ISOMERIC PENTANOIC ACIDS, ESTERS PREPARED THEREFROM, AND THEIR USE AS LUBRICANTS

[75] Inventors: Helmut Bahrmann, Hamminkeln; Wolfgang Greb; Georg Dämbkes, both of Dinslaken; Peter Heymanns, Essen; Heinz Kalbfell, Schermbeck; Peter Lappe, Dinslaken; Helmut Springer, Oberhausen; Eberhard von Mülmann, Oberhausen; Jürgen Weber, Oberhausen; Ernst Wiebus, Oberhausen; Carl D. Frohning, Wesel; Harald Kappesser, Oberhausen, all of Germany

[73] Assignee: Hoechst Aktiengesellschaft, Germany

[21] Appl. No.: 311,557

[22] Filed: Sep. 23, 1994

[30] Foreign Application Priority Data

Sep. 30, 1993 [DE] Germany .................. 43 33 323.0

[51] Int. Cl.⁶ ............... C07C 53/126; C07C 53/128; C07C 45/50
[52] U.S. Cl. ................................ 560/239; 562/544
[58] Field of Search .................. 560/239; 562/544

[56] References Cited

U.S. PATENT DOCUMENTS 4,113,442  9/1978  Hoff et al. ............... 44/397
4,681,972  7/1987  Kaltenbronn et al. ............ 560/29

*Primary Examiner*—Arthur C. Prescott
*Attorney, Agent, or Firm*—Jordan B. Bierman; Bierman and Muserlian

[57] ABSTRACT

Isomeric mixtures of pentanoic acids are prepared by subjecting butene-1/butene-2 mixtures to hydroformylation to form aldehyde mixtures, followed by oxidation of the aldehyde mixtures which have been separated off from the reaction product. The hydroformylation is carried out in a heterogeneous system in the presence of rhodium catalysts which are dissolved in water. The mixture of isomeric 5 carbon monocarboxylic acids produced, when esterified with polyhydric alcohols, yields mixtures of isomeric esters which are useful as lubricants for refrigerant compressors operated with chlorine-free, at least partly fluorinated hydrocarbons as the refrigerant.

20 Claims, No Drawings

MIXTURES OF ISOMERIC PENTANOIC ACIDS, ESTERS PREPARED THEREFROM, AND THEIR USE AS LUBRICANTS

This Application claims the priority of German P 43 33 323.0, filed Sep.30, 1994.

This invention relates to mixtures of isomeric, aliphatic monocarboxylic acids having 5 carbon atoms, a process for their preparation, the esters obtained from these acids, and the use of these esters as lubricants, especially for refrigeration compressors wherein the refrigerants are chlorine-free, partly fluorinated hydrocarbons.

BACKGROUND OF THE INVENTION

Refrigerant compressors are widely used in cooling devices for the industrial, commercial, and private sectors. These devices operate with mechanical compressors which compress the refrigerant, liquify it in the condenser by cooling with air, water, or another medium, and evaporate it in the evaporator, thereby absorbing heat from the medium to be cooled. The refrigerant employed for large-scale plants is primarily ammonia; fluorochlorohydrocarbons, such as dichlorodifluoromethane or chlorotrifluoromethane, are also used for large scale plants, and principally for commercial refrigeration plants and domestic appliances.

Highly refined (generally naphthene-based) mineral oils similar to white oil are used for the lubrication of refrigerant compressors. Alkylaromatics and poly-alpha-olefins are employed as synthetic oils for this purpose.

The function of the lubricating oils is to lubricate the moving components of the compressor, remove heat from the hot components of the compressor, and seal off the compression space and the valves. These requirements also determine the properties which the lubricating oils must satisfy. They must withstand thermal stresses and also remain capable of flowing at evaporator temperatures. Moreover, it should be remembered that the lubricating oils may be discharged from the compression space into the refrigerant circulation and cannot be removed completely by subsequent oil separators. They must therefore be miscible with the refrigerant over wide ranges of temperature and concentration, so that recycling of lubricating oil which has entered the refrigerant circulation in the compressor is ensured.

Fluorochlorohydrocarbons have for some time been suspected of damaging the ozone layer of the Earth's atmosphere. Efforts are therefore being made to limit them to those uses where they cannot be replaced. Attempts are otherwise being undertaken to replace them by substances which have an equivalent action but are harmless. Chlorine-free, partly fluorinated hydrocarbons, such as 1,1,1,2-tetrafluoroethane, 1,1,1,2,3,3,3-heptafluoropropane, pentafluoroethane, 1,1,1,3,3,3-hexafluoropropane and trifluoromethane, will be employed in the future as refrigerants. These substances are distinguished by high heat stability and desirable thermodynamic properties in the temperature ranges in which refrigerant compressors operate.

The chlorine-free aliphatic fluorohydrocarbons are miscible with the lubricants used to date for refrigeration plants only to a slight extent. The two classes of substances form two-phase mixtures over wide concentration ranges, so that recycling of the lubricant discharged from the compressor is considerably impeded, especially at low temperatures. It has therefore been necessary to discover novel lubricants which are compatible with the chlorine-free refrigerants. Amongst these novel lubricants, esters obtained from monocarboxylic acids and di- or polyhydric alcohols have proven outstandingly suitable (cf. DE 40 06 827 Al). More recent studies are aimed at developing lubricants from readily available raw materials and, in view of the number of new refrigerants, with a large variety of fluorohydrocarbons.

Thus, the object of the Invention is to provide inexpensive starting materials which can be converted by the conventional route into lubricants which can be used with a wide variety of refrigerants.

SUMMARY OF THE INVENTION

Surprisingly, it has been found that selected mixtures of isomeric carboxylic acids give, together with di- or polyhydric aliphatic alcohols, ester lubricants which combine high profitability with diverse usability.

The invention comprises mixtures of isomeric pentanoic acids obtained by hydroformylation of butene-1/butene-2 mixtures in a heterogeneous reaction system. The catalysts are rhodium compounds containing water-soluble phosphines bonded as a complex, and the reaction is carried out at temperatures of 70° to 150° C. under pressures of 0.4 to 30 MPa to give aldehyde mixtures, the resulting aldehyde mixtures are removed from the hydroformylation product, and the product is oxidized to give the desired mixture of isomeric pentanoic acids.

DETAILED DESCRIPTION OF THE INVENTION

The mixtures comprising butene-1 and butene-2 which are employed as the starting materials of the present invention are necessarily produced in substantial quantities as refinery byproducts during preparation of automobile fuels and during preparation of ethylene by thermal cracking of higher hydrocarbons. They are isolated from the 4-carbon fractions of pyrolysis cracking by extraction of 1,3-butadiene by a selective solvent and subsequent removal of the isobutene, preferably by conversion into methyl butyl ether. The pyrolysis product which has been freed from butadiene is called Raffinate I. If the isobutene has also been removed, the result is Raffinate II.

Alternatively, the butadiene can be partly hydrogenated to butenes; after removal of the isobutene, a butene-1/butene-2 mixture, which is particularly suitable for further processing to 5 carbon alcohols is obtained. Finally, there has recently also been a trend, toward hydrogenating the extracted butadiene to butane which is recycled to the cracking stage, to increase the yield of ethylene and propylene.

According to the invention, mixtures comprising butene-1 and butene-2, for example Raffinate II, as well as those of a different origin and composition, are hydroformylated. In this reaction, butene-1 is preferentially converted into a mixture which comprises primarily n-valeraldehyde and, in a minor amount, i-valeraldehyde. The reaction proceeds under conditions which largely exclude isomerization of butene-1 to butene-2. Unreacted olefins, mainly butene-2, can be recycled to a second hydroformylation stage to carry the reaction to completion.

The hydroformylation is carried out according to the invention as a heterogeneous reaction in a two-phase system, a reaction which is described, for example, in DE-C 26 27 354. This process is characterized by the presence of an organic phase which comprises the starting olefins and the reaction product, and an aqueous phase in which the catalyst is dissolved. Water-soluble rhodium complex compounds, which contain water-soluble phosphines as ligands, are employed as catalysts. The phosphines include, in particular, triarylphosphines, trialkylphosphines, and arylated and alkylated diphosphines, the organic radicals of which are substituted by sulfonic acid or carboxyl groups. Their preparation is known, for example, from DE-C 26 27 354 and DD Patent 259 194. The reaction of the butenes is carried out at temperatures of 70° to 150° C., preferably 100° to 130° C., under pressures in the range of 0.4 to 30, in particular 1 to 10 MPa; water gas, which comprises carbon monoxide and hydrogen in a volume ratio of 1:10 to 10:1, is used. The rhodium concentration is 20 to 1000 ppm by weight, preferably 50 to 500 ppm by weight, based on the aqueous catalyst solution. 4 to 100 mol of water-soluble phosphine are employed per mol of rhodium. The volume ratio of aqueous to organic phase is 0.1 to 10:1.

The butene conversion per unit time is increased significantly if a phase transfer reagent (solubilizing agent) is added to the aqueous catalyst solution. This changes the physical properties of the interfaces between the two liquid phases and facilitates transfer of the organic reactant into the aqueous catalyst phase.

Compounds in which the hydrophilic groups are ionic (anionic or cationic) or nonionic are known solubilizing agents. Anionic compounds include sodium salts, potassium salts, and ammonium salts of carboxylic acids having 8 to 20 carbon atoms, in particular of saturated fatty acids having 12 to 18 carbon atoms, as well as alkylsulfates, alkylbenzenesulfonates, and alkylbenzene phosphates. Examples of cationic solubilizing agents are tetraalkylammonium and N-alkylpyridinium salts. The nonionic phase transfer reagents cannot dissociate into ions in aqueous solution. They include alkylpolyethyleneglycols, alkylphenylpolyethyleneglycols, fatty acid alkylolamides, and trialkylaminooxides. Finally, ampholytes, such as aminocarboxylic acids, betaines, and sulfobetaines, are also used as solubilizing agents.

Cationic solubilizing agents of the formula $[A-N(R^1R^2R^3)]^+E^-$, in which A is a straight or branched chain alkyl radical having 6 to 25 carbon atoms, $R^1$, $R^2$, and $R^3$ are the same or different and are straight or branched chain alkyl radicals having 1 to 5 carbon atoms, and E is an anion, in particular sulfate, tetrafluoroborate, acetate, methosulfate, benzenesulfonate, alkylbenzenesulfonate, toluenesulfonate, lactate, or citrate, have proven particularly suitable. When the hydroformylation has ended, the aldehyde mixture is separated from the catalyst, the unreacted reactants, and the other reaction products by simple phase separation.

In the subsequent reaction stage, the aldehyde mixtures are oxidized to a mixture of isomeric pentanoic acids. The reaction can be carried out in known manner by treatment of the aldehydes with oxygen in the pure form or as a mixture with inert gases in the absence—or preferably, in the presence—of catalysts. Possible catalysts are chiefly salts of the transition metals, in particular salts of cobalt and manganese, as well as of chromium, iron, copper, nickel, silver, and vanadium. To avoid degradation and secondary reactions, the oxidation is carried out at the lowest possible temperatures. Furthermore, the selectivity of the reaction can be improved by addition of alkali metal salts of weak carboxylic acids, for example potassium pentanoate. For purification, the acid mixture is distilled. It is outstandingly suitable as an acid component in ester lubricants.

The esters contain, as the alcohol component, di- or polyhydric alcohols. Examples of dihydric alcohols are ethylene glycol, diethylene glycol, triethylene glycol, propane-1,2-diol, dipropylene glycol, tripropylene glycol, propane-1,3-diol, butane-1,3-diol, butane-1,4-diol, neopentylglycol, hexane-1,6-diol, 3(4),8(9)bis(hydroxymethyl)tricyclo[5.2.1.0$^{2.6}$]decane, and 1,4-dimethylolcyclohexane Of the polyhydric alcohols, the tri- and tetrahydric are of particular importance; trimethylolpropane (2-ethyl-2-hydroxymethyl-1,3-propanediol), glycerol, and pentaerythritol (2,2-bis(hydroxymethyl)-1,3-propanediol) may be mentioned as examples. The di- and polyhydric alcohols are prepared starting from known individual processes. Esters of neopentylglycol with monocarboxylic acids are of particular importance.

The esters are prepared in known manner from the above-mentioned acids and alcohols in the presence of acid catalysts. Suitable catalysts include mineral acids, such as sulfuric acid and phosphoric acid, and acid salts thereof; furthermore, trialkylphosphates, triaryl phosphates, and p-toluenesulfonic acid are all suitable. To achieve as complete a reaction as possible, it is advisable to use one of the reactants in excess and/or to separate out the water of reaction by distillation, if appropriate with addition of an agent which forms an azeotrope, such as benzene, toluene, or cyclohexane.

The lubricants used according to the invention have good miscibility with the chlorine-free, partly fluorinated hydrocarbons employed as refrigerants, even at $-40°$ C. i.e. in the temperature ranges which can occur in compression refrigeration plants. Their viscosity is between about 10 and 100 mm$^2$/seconds at 40° C., and thus corresponds to the requirements imposed on the lubricant for the field of use described above. They have, moreover, excellent heat stability when atmospheric oxygen and moisture are excluded, i.e. under conditions which must be fulfilled in refrigerant circulation. The esters are not hygroscopic. They can, therefore, be dried without great difficulty. Residual moisture contents, which, according to German Standard DIN 51 503, should not exceed 35 ppm, can be achieved without problems. The isomeric esters used as lubricants can be employed as such or else as a mixture with two or more esters of different chemical composition.

The following Examples illustrate the invention but do not limit it.

Example 1

A mixture of isomeric pentanoic acids (4.2 mol) is reacted with pentaerythritol (1 mol), in the presence of p-toluenesulfonic acid (0.01 mol) as the catalyst, and cyclohexane, to remove the water of reaction as an azeotrope, at 140° C. over a period of 4 hours. The reaction product is neutralized with sodium hydroxide solution (5% NaOH by weight). The aqueous and organic phase are separated, the organic phase is washed with water, and additional sodium hydroxide solution (5% NaOH by weight) is added until a pH of 9 to 10 is established. The organic phase is again separated out, washed with water, and finally distilled.

Criteria which allow the suitability of the ester mixture as a lubricant to be evaluated are its viscosity and its miscibility with 1,1,1,2-tetrafluoroethane (R 134a) as a representative of the non-chlorinated fluorohydrocarbon refrigerants. The viscosity of the ester mixture is measured in an Ubbelohde viscometer at 40° C.

To test the miscibility of the ester mixture with the refrigerant, a defined amount of ester (0.2 to 3.0 g) is introduced into a glass tube having a capacity of about 10 ml. After immersion in liquid nitrogen, between 6 and 3 g of the refrigerant, depending on the concentration to be established, is condensed into the tube. The glass tube is then evacuated, sealed by fusion and passed, while containing a specific mixture, through a temperature range of −40° C. to +80° C. When two phases form or when clouding starts, the separation point, i.e. a point on the limit curve of the mixing diagram, can be determined. The limit curve of the miscibility gap is then obtained from all the separation points found.

Result: the ester mixture has a kinematic viscosity of 16.9 mm$^2$/s at 40° C. and shows no miscibility gaps with R 134a down to −30° C.

While only a single specific embodiment of the present Invention has been expressly disclosed, it is, nonetheless, to be broadly construed, and not to be limited except by the character of the claims appended hereto.

What is claim is:

1. An isomeric mixture of pentanoic acids which results from hydroformylation of a butene-1/butene-2 mixture in a heterogeneous reaction system, comprising an aqueous phase and an organic phase, in the presence of a catalyst in said aqueous phase which comprises a rhodium compound containing a water-soluble phosphine bonded as a complex, said hydroformylation being carried out at 70° to 150° C. under 0.4 to 30 MPa to form an aldehyde mixture in a hydroformylation product, separation of said aldehyde mixture from said hydroformylation product, and oxidation of said aldehyde mixture.

2. The isomeric mixture of claim 1 wherein said hydroformylation is effected in a first stage and a second stage, said first stage being carried out at 100° to 130° under a first pressure of 1 to 10 MPa.

3. The isomeric mixture of claim 1 wherein said rhodium is present in a catalyst concentration of 20 to 1000 ppm by weight, based on said aqueous phase.

4. The isomeric mixture of claim 3 wherein said catalyst concentration is 50 to 500 ppm by weight, based on said aqueous phase.

5. The isomeric mixture of claim 1 wherein said catalyst comprises 4 to 400 mol of said phosphine per mol of said rhodium.

6. The isomeric mixture of claim 1 wherein said aqueous solution comprises a phase transfer reagent.

7. The isomeric mixture of claim 6 wherein said phase transfer reagent is selected from the group consisting of sodium, potassium, and ammonium salts of carboxylic acids having 8 to 20 carbon atoms, alkyl sulfates, alkylbenzenesulfonates, alkylbenzenephosphates, salts of tetraalkylammonium, and N-alkylpyridinium, alkylpolyethyleneglycols, alkylphenylpolyethyleneglycols, fatty acids alkylolamides, trialkylaminooxides, aminocarboxylic acids, betaines, and sulfobetaines.

8. The isomeric mixture of claim 6 wherein said phase transfer reagent is of the formula

wherein A is a straight or branched chain alkyl radical having 6 to 25 carbon atoms, $R^1$, $R^2$, and $R^3$ are individually straight or branched chain alkyl radicals having 1 to 5 carbon atoms, and E is an anion.

9. The isomeric mixture of claim 8 wherein E is selected from the group consisting of sulfate, tetrafluoroborate, acetate, methosulfate, benzenesulfonate, alkylbenzenesulfonate, toluenesulfonate, lactate, and citrate.

10. The isomeric mixture of claim 1 wherein said oxidation takes place in the presence of an oxidation catalyst comprising salts of transition metals.

11. The isomeric mixture of claim 1 wherein said oxidation takes place in the presence of an oxidation catalyst selected from the group consisting of salts of cobalt, manganese, chromium, iron, copper, nickel, silver, and vanadium.

12. The isomeric mixture of claim 1 wherein said hydroformylation takes place in the presence of hydrogen and carbon monoxide in a volume ratio of 1:10 to 10:1.

13. The isomeric mixture of claim 1 wherein said aqueous phase and said organic phase are present in a volume ratio of 0.1:1 to 10:1.

14. An ester mixture which is the reaction product of the pentanoic acids of claim 1 with at least one alcohol.

15. The ester mixture of claim 14 wherein said alcohol is pentaerythritol.

16. The ester mixture of claim 14 wherein said alcohol is polyhydric.

17. The ester mixture of claim 16 wherein said alcohol is selected from the group consisting of ethylene glycol, diethylene glycol, triethylene glycol, propane-1,2-diol, dipropylene glycol, tripropylene glycol, propane-1,3-diol, butane-1,3-diol, butane-1,4-diol, neopentyl glycol, hexane-1,6-diol, and 3(4), 8(9)-bis(hydroxymethyl)tricyclo[5.2.1.0$^{2.6}$]decane.

18. The ester mixture of claim 16 wherein said alcohol is trihydric or tetrahydric.

19. The ester mixture of claim 18 wherein said alcohol is selected from the group consisting of trimethylglycolpropane, glycerol, and pentaerythritol.

20. The ester mixture of claim 16 wherein said alcohol is neopentylglycol and said acids are monocarboxylic.

* * * * *